United States Patent
Podolski et al.

(10) Patent No.: US 9,616,034 B2
(45) Date of Patent: Apr. 11, 2017

(54) TRANS-CLOMIPHENE AND ITS ANALOGUES AS AGENTS THAT INCREASE BONE MINERAL DENSITY

(71) Applicant: REPROS THERAPEUTICS INC., The Woodlands, TX (US)

(72) Inventors: Joseph S. Podolski, The Woodlands, TX (US); Kuang Hsu, The Woodlands, TX (US); Ronald D. Wiehle, Houston, TX (US); Greg Fontenot, The Woodlands, TX (US); Jaye Thompson, The Woodlands, TX (US)

(73) Assignee: REPROS THERAPEUTICS INC., The Woodlands, TX (US)

( * ) Notice: Subject to any disclaimer, the term of this patent is extended or adjusted under 35 U.S.C. 154(b) by 0 days.

(21) Appl. No.: 14/896,043

(22) PCT Filed: Jun. 3, 2014

(86) PCT No.: PCT/US2014/040704
§ 371 (c)(1),
(2) Date: Dec. 4, 2015

(87) PCT Pub. No.: WO2014/197477
PCT Pub. Date: Dec. 11, 2014

(65) Prior Publication Data
US 2016/0128953 A1    May 12, 2016

Related U.S. Application Data

(60) Provisional application No. 61/831,542, filed on Jun. 5, 2013.

(51) Int. Cl.
*A61K 31/135* (2006.01)
*A61K 31/138* (2006.01)
(52) U.S. Cl.
CPC .................. *A61K 31/138* (2013.01)

(58) Field of Classification Search
None
See application file for complete search history.

(56) References Cited

U.S. PATENT DOCUMENTS

| 8,247,456 B2 * | 8/2012 | Podolski | A61K 31/138 |
| | | | 514/646 |
| 2007/0004626 A1 | 1/2007 | Masuda | |
| 2009/0215907 A1 | 8/2009 | Podolski | |

FOREIGN PATENT DOCUMENTS

WO    2013/130832 A1    9/2013

OTHER PUBLICATIONS

Eastell, R., "Long-Term Effects of Anastrozole on Bone Mineral Density: 7-year Results form the ATAC Trial," Annals of Oncology, vol. 22, No. 4, pp. 857-862 (Apr. 2011).
Eastell, R., "Effect of an Aromatase Inhibitor on BMD and Bone Turnover Markers: 2-Year Results of the Anastrozole, Tamoxifen, Alone or in Combination (ATAC) Trial (18233230)," Journal of Bone and Mineral Research, vol. 21, No. 8, pp. 1215-1223 (May 22, 2006).
International Search Report of PCT/US2014/040704 dated Oct. 15, 2014.
Written Opinion of PCT/US2014/040704 dated Oct. 15, 2014.

* cited by examiner

*Primary Examiner* — Heidi Reese
(74) *Attorney, Agent, or Firm* — Morgan, Lewis & Bockius LLP (57) ABSTRACT

The present invention relates to the administration of compositions comprising trans-clomiphene or an analog or salt thereof, for inhibiting bone resorption and bone turnover in a subject. The invention is also directed to methods for increasing bone mineral density in a subject and preventing or treating a bone related disorder in a subject comprising administering to the subject an effective amount of trans-clomiphene or an analog or salt thereof.

12 Claims, 6 Drawing Sheets

TRANS-CLOMIPHENE AND ITS ANALOGUES AS AGENTS THAT INCREASE BONE MINERAL DENSITY

CROSS-REFERENCE TO RELATED APPLICATIONS

The application claims the benefit of U.S. Provisional Application No. 61/831,542, filed Jun. 5, 2013, the contents of which are incorporated herein by reference.

FIELD OF THE INVENTION

The present invention relates to compositions and methods for inhibiting bone resorption and bone turnover. Specifically, the present invention relates to the use of the selective estrogen receptor modulator trans-clomiphene or an analogue or salt thereof to increase bone mineral density and treat or prevent osteoporosis and/or osteopenia in this patient group.

BACKGROUND

Bone mineral loss can result from a variety of causes including chronic conditions such as Cushing's syndrome, homocystinuria, hypercalciuria, and hyperprolactinemia. Alternatively, bone mineral loss is also associated with the normal aging process and accompanying loss of gonadal function in both females and males. Ostoeoporosis is characterized by significant reductions in bone mineral density, structural deterioration of bone tissue and enhanced susceptibility to bone fracture. This condition is generally preceded by osteopenia, a condition defined by the World Health Organization as a bone mineral density that is at least one standard deviation below that of an average 30-year old white woman. The frequency of these disorders increase with age in both males and females as does susceptibility to bone fractures, particularly of the hip.

In males, androgen deficiency is associated with a variety of symptoms including low bone mass. Indeed, the incidence of osteopenia, osteoporosis in this patient group is relatively high with a correspondingly high bone fracture rate. Testosterone plays a major role in bone mineral density (BMD); however, the effect of testosterone replacement on BMD remains controversial with several studies indicating that the effects of testosterone replacement on bone does not differ significantly from placebo (Snyder P J et al., J Clin Endocrinol Metab. 1999; 84:1966-1972). Other studies have reported a slight increase in BMD during testosterone replacement therapy which is thought to result from the conversion of testosterone into estradiol.

In the course of drug development, the inventors observed that treatment of men with isolated trans-clomiphene was accompanied by a significant reduction in CTX (C-terminal crosslinking telopeptide of type I collagen), an established biomarker of bone resorption, which is negatively correlated with BMD, presumably because reduced bone turnover provides a correspondingly increased opportunity for bone mineralization (Meunier and Boivin, Bone 21:373-377 (1997)). Thus, trans-clomiphene and its triphenylalkylene analogues provide a safe and effective class of compounds for the prevention and treatment of osteoporosis and/or osteopenia.

SUMMARY

Figure 4:
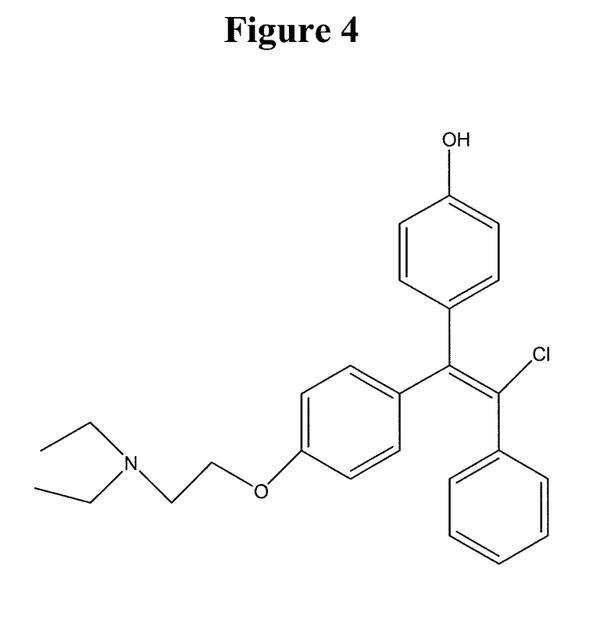
FIG. 4 shows the chemical structure of (E)-4-OH-Clomiphene.
Figure 5:
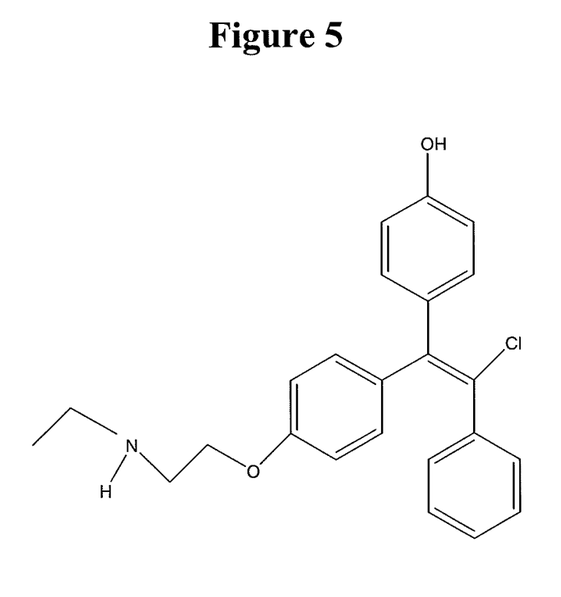
FIG. 5 shows the chemical structure of (E)-4-OH-DE-Clomiphene.
Figure 6:
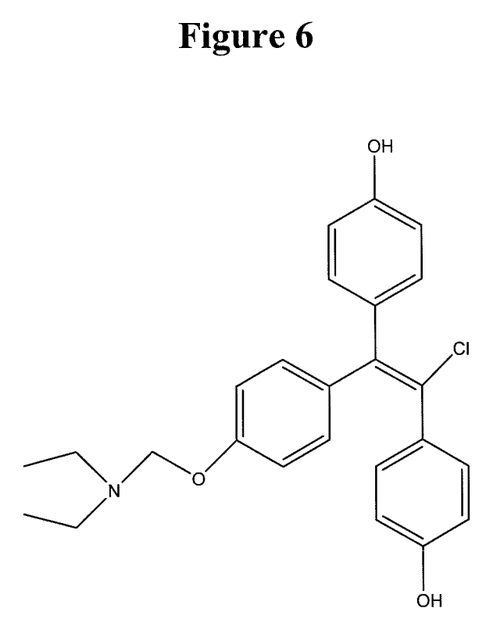
FIG. 6 shows the chemical structure of (E)-4,4'-di-OH Clomiphene.

In several embodiments, the present invention is directed to methods for inhibiting bone resorption comprising administering to a subject an amount of a composition comprising trans-clomiphene, an analogue thereof or a pharmaceutically acceptable salt thereof, the composition preferably being substantially free of cis-clomiphene, effective to reduce the level of a marker of bone resorption such as C-terminal crosslinking telopeptide of type I collagen (CTX). Preferably, the amount of trans-clomiphene or analogue or salt thereof is effective to decrease the serum level of CTX by at least 5%, more preferably by at least 10%, most preferably by at least 15% compared to serum levels absent treatment (e.g. compared to baseline levels). The subject may be a human male or female. In one embodiment, the subject is a human male with low or low normal testosterone (e.g. below about 400 ng/dl). In another embodiment, the subject is a secondary hypogonadal human male. Preferred trans-clomiphene analogs for use according to the invention are (E)-4-OH-Clomiphene (FIG. 4), (E)-4-OH-desethyl Clomiphene (FIG. 5) and (E)-4,4'-di-OH Clomiphene (FIG. 6).

In related embodiments, the present invention is directed to methods for inhibiting bone turnover comprising administering to a subject an amount of a composition comprising trans-clomiphene, an analogue thereof or a pharmaceutically acceptable salt thereof, the composition preferably being substantially free of cis-clomiphene, effective to (i) reduce the level of a marker of bone resorption such as CTX and (ii) reduce the level of a marker of bone formation such as N-terminal extension of procollagen type 1 (P1NP). Preferably, the amount of trans-clomiphene or analogue or salt thereof is effective to decrease the serum level of CTX by at least 5%, more preferably by at least 10%, most preferably by at least 15% and to decrease the serum level of P1NP by at least 15%, preferably by at least 20%, most preferably by at least 25% compared to serum levels absent treatment. The subject may be a human male or female. In one embodiment, the subject is a human male with low or low normal testosterone (e.g. below about 400 ng/dl). In another embodiment, the subject is a secondary hypogonadal human male.

The present invention is also related to a method for increasing or maintaining bone mineral density in a subject comprising administering to the subject an effective amount of a composition comprising trans-clomiphene, an analogue thereof or a pharmaceutically acceptable salt thereof, the composition preferably being substantially free of cis-clomiphene, wherein bone mineral density is maintained or increased. Preferably, the amount of trans-clomiphene or analogue or salt thereof is effective to increase total hip BMD by at least 1.2% compared to baseline (i.e. pretreatment) levels. The subject may be a human male or female diagnosed with osteopenia or osteoporosis or at risk for developing osteopenia or osteoporosis. In a preferred embodiment, a human male with osteopenia or osteoporosis or at risk for developing osteopenia or osteoporosis is administered a composition comprising trans-clomiphene or an analogue or pharmaceutically acceptable salt thereof wherein the composition is substantially free of cis-clomiphene, whereby bone mineral density is increased in the male. In a particularly preferred embodiment, the human male also has a low or low normal testosterone level. In another preferred embodiment, a human male with a normal testosterone level (e.g. above 300 ng/dl) is administered a composition comprising trans-clomiphene or an analogue or pharmaceutically acceptable salt thereof, wherein the composition is substantially free of cis-clomiphene, whereby bone mineral density is maintained in the male.

The present invention also provides a method of treating a bone-related disorder in a subject comprising administering to a subject in need of such treatment a composition comprising an amount of trans-clomiphene, an analogue thereof or a pharmaceutically acceptable salt thereof, effective to increase bone mineral density in the subject, the composition preferably being substantially free of cis-clomiphene. Preferably, the amount is effective to increase BMD at the hip (total hip and/or femoral neck) by at least 1%. In some embodiments, the subject in need thereof is a human with a BMD characteristic of osteopenia or osteoporosis and trans-clomiphene or an analogue or salt thereof is administered in an amount and for a treatment period effective to increase BMD into the normal range in the subject.

In other related embodiments, the present invention is related to methods for preventing and/or treating osteopenia or osteoporosis in a subject in need thereof comprising administering to the subject an effective amount of a composition comprising trans-clomiphene, an analogue thereof or a pharmaceutically acceptable salt thereof, the composition preferably being substantially free of cis-clomiphene. The subject may be a human male or female diagnosed with osteopenia or osteoporosis or at risk for developing osteopenia or osteoporosis. In a preferred embodiment, a human male with osteopenia or osteoporosis or at risk for developing osteopenia or osteoporosis is administered a composition comprising trans-clomiphene or an analogue or pharmaceutically acceptable salt thereof wherein the composition is substantially free of cis-clomiphene. In a particularly preferred embodiment, the human male has a low or low normal a testosterone level (e.g. about 400 ng/dl or lower). Preferably, the amount of trans-clomiphene or analogue or salt thereof is effective to decrease the serum level of CTX by at least 5%, preferably at 10%, more preferably at least 15% and/or increase total hip BMD by at least 1.2% compared to baseline (i.e. pretreatment) levels.

The present invention also provides a method for monitoring the physiological response of a subject to trans-clomiphene comprising administering a composition comprising trans-clomiphene or an analogue or salt thereof and detecting the level of one or more markers of bone resorption wherein a reduction of at least about 5%, about 10%, about 15% or about 20% or more in the level of a marker of bone resorption compared to pre-treatment levels or normal levels for the patient population indicates the treatment is effective. The method may alternatively or additionally comprise detecting the level of one or more markers of bone formation wherein a reduction of at least about 10%, about 15%, about 20%, about 25% or about 30% or more in the level of a marker of bone formation compared to pre-treatment levels or normal levels for the patient population indicates the treatment is effective. Preferably, baseline measurements of the one or more biomarkers of bone resorption and/or the one or more biomarkers of bone formation are made prior to initiating treatment. In related embodiments, the method further comprises adjusting the dose of trans-clomiphene or an analogue thereof (e.g. to a higher dosage if the change in bone resorption is less than desired and to a lower dosage if the change in bone resorption is higher than desired).

The present invention also provides a combination therapy whereby a composition comprising an effective amount of trans-clomiphene or an analogue or pharmaceutically acceptable salt thereof, is sequentially, separately or simultaneously co-administered with one or more additional agents. In some embodiments, the trans-clomiphene or an analogue or salt thereof is co-administered with one or more agents designed to further reduce the level of a marker of bone resorption or to increase the level of a marker of bone formation. In one aspect, trans-clomiphene or an analogue or salt thereof and an antiresorptive drug are administered to a subject. Antiresorptive drugs include, without limitation, oral bisphosphonates such as alendronate (Fosamax), risedronate (Actonel) and ibandronate (Boniva) and injectible bisphosphonates such as zoledronic acid (Reclast). In other aspects, trans-clomiphene or an analogue or salt thereof and an anabolic drug are administered to a subject. Anabolic drugs include, without limitation, parathyroid hormone (PTH) which is administered by injection, including recombinant forms of PTH such as teriparatide, which comprises amino acids 1-34 of the human parathyroid hormone sequence (the complete molecule contains 84 amino acids).

Preferred dosages of trans-clomiphene or an analogue or salt thereof include 25 mg to 100 mg, 25 mg to 50 mg, 12.5 mg to 100 mg, 12.5 mg to 50 mg, 12.5 mg to 25 mg, 5 mg to 20 mg, and 5 mg to 15 mg trans-clomiphene or an analogue or salt thereof. Preferably trans-clomiphene is administered daily or every other day, but may also be administered periodically such as weekly, bi-weekly or even monthly. Preferably periodic administration of trans-clomiphene is preceded by daily administration for a period of time sufficient to achieve therapeutic levels of testosterone.

Trans-clomiphene or an analogue or salt thereof according to the methods described herein is administered for a period of time sufficient to achieve the desired result. In one aspect, trans-clomiphene or an analogue or salt thereof is administered for treatment period of at least 3 months, at least 6 months, at least 12 months or even at least 2, 3, 4, or 5 years. In any of the methods described herein, the level of one or more markers of bone resorption (e.g. CTX) is reduced by about 5%, 10%, 15%, 20%, 25% or more for at least 2 weeks, at least 3 weeks, at least 1 month, at least 6 weeks, at least 3 months, at least 6 months, at least one year, or more compared to pre-treatment levels or normal levels for that patient group. In any of the methods described herein, the level of one or more markers of bone formation such as P1NP is reduced by about 10%, 15%, 20%, 25%, 30% or more for at least 2 weeks, at least 3 weeks, at least 1 month, at least 6 weeks, at least 3 months, at least 6 months, at least one year, or more compared to pre-treatment levels or normal levels for that patient group. By way of example, the level of bone resorption marker or bone formation marker by 3 months after initiation of treatment is reduced by e.g. at least 5%, at least 10%, at least 15% or at least 20% compared to the pre-treatment levels or normal levels for that patient population.

DETAILED DESCRIPTION

The present invention is based, at least in part, on the surprising discovery that trans-clomiphene significantly reduces serum biomarkers of bone resorption such as CTX and reduces serum biomarkers of bone formation such as P1NP. The reduction in bone turnover is shown to correspond with an increase in bone mineral density (BMD). Clomiphene is thought to exert its effects at the level of the hypothamus-pituitary axis by specifically stimulating secretion of the gonadotropic hormones LH and FSH. In males, the increase in gonadotropins is associated with increased testosterone levels. A corresponding increase in estrogen levels follows as some amount of the testosterone is aromatized. The effect of estrogen on bone mineral density (BMD) is well established; the effect of androgens on BMD remains controversial. Surprisingly, trans-clomiphene appears to inhibit bone turnover through a different mechanism than testosterone, as administration of exogenous testosterone had no effect on the level of a marker of bone formation, whereas a significant reduction of the same marker was observed following treatment with trans-clomiphene. The activity of trans-clomiphene in inhibiting bone resorption and bone turnover is associated with increases in BMD and therefore renders the present compositions useful for treating a variety of bone related disorders.

In several embodiments the present invention provides methods for inhibiting bone resorption in a subject by administering a composition comprising an amount of trans-clomiphene or a triphenylalkylene analog or salt thereof in an amount effective to reduce the serum level of one or biomarkers of bone resorption such as CTX. Preferably, the composition is substantially free of the cis-isomer and comprises trans-clomiphene or a metabolite selected from (E)-4-OH-clomiphene (FIG. 4) and (E)-4-OH-desethyl-clomiphene (FIG. 5). The subject may be a human male or female.

Biomarker levels indicative of bone resorption may be measured to gauge the physiological response in a subject to trans-clomiphene or an analogue or salt thereof. Such markers include, without limitation, C-terminal telopeptide of type 1 collagen (CTX), N-terminal telopeptide of type 1 collagen (NTX), deoxypyridinoline (DPD), pyridinoline, urinary hydroxyproline, galactosyl hydroxylysine, and tartrate-resistant acid phosphatase. Preferably, the serum level of CTX is measured. The amount of trans-clomiphene (or an analogue or salt thereof) is preferably effective to reduce the level of one or more markers of bone resorption such as CTX by at least about 5%, about 10%, about 15% about 20% or more compared to the level of the bone resorption marker prior to administering trans-clomiphene (or an analogue or salt thereof).

In other embodiments, the present invention provides methods for inhibiting bone turnover in a subject by administering a composition comprising an amount of trans-clomiphene or an analog or salt thereof in an amount effective to (i) reduce the serum level of one or biomarkers of bone resorption such as CTX and (ii) reduce the serum level of one or more biomarkers of bone formation such as N-terminal extension of procollagen type 1 (P1NP). Preferably, the composition comprises trans-clomiphene and is substantially free of the cis-isomer. P1NP is produced by osteoblasts and measures bone formation, with lower levels of P1NP indicating lower bone turnover. Reductions in bone turnover appear to allow for increased opportunity for bone mineralization throughout the body (Meunier and Boivin, Bone 21:373-377 (1997)) and a reduction in the risk of fractures.

Biomarker levels indicative of bone formation may be measured to gauge the response in a subject to trans-clomiphene or an analogue or salt thereof. Such markers include, without limitation, P1NP, bone-specific alkaline phosphatase (BSAP) and osteocalcin (OstCa). Preferably, the serum level of P1NP is measured. The amount of trans-clomiphene (or an analogue or salt thereof) is preferably effective to reduce the level of one or more markers of bone formation such as P1NP by at least about 10%, about 15%, about 20%, about 25%, about 30% or more compared to the level of the bone formation marker prior to administering trans-clomiphene (or an analogue or salt thereof).

In other aspects, the present invention provides a method for increasing bone mineral density (BMD) in a subject comprising administering to the subject an amount of a composition comprising trans-clomiphene or an analogue or salt thereof effective to increase BMD in the subject. In related embodiments, the amount is effective to reduce the level of a marker of bone resorption and optionally also reduce the level of a maker of bone formation. Preferably, the composition is substantially free of the cis-isomer and comprises trans-clomiphene. BMD can be measured as "total body" (head, trunk, arms and legs) or at the hip (e.g. total hip and/or femoral neck), spine, wrist, finger shin bone and/or heel, but is preferably measured as hip BMD. BMD is typically compared to the peak density of a 30 year old healthy adult creating a so-called "T-score." A subject's BMD score may also be compared with an age-matched bone density. The difference between a subject's BMD and that of a healthy young adult is conventially referred to in terms of the multiple of a "standard deviation" which typically equals about 10% to about 12% decrease in bone density. A BMD value within 1 standard deviation of the young adult reference mean (T-score of at least −1) is "normal". Osteopenia is indicated by a BMD value more than 1 standard deviation below the young adult mean, but less than 2 standard deviations (T score is between −1 and −2.5). A t-score of more than 2.5 standard deviations below the norm indicates a diagnosis of osteoporosis. (World Health Organization Scientific Group on the Prevention and Management of Osteoporosis, WHO Technical Report Series; 921, Geneva, Switzerland (2000)). Compositions of the invention may be administered to a subject to improve BMD regardless of the subject's T-score. Preferably, the amount of trans-clomiphene or analogue or salt thereof is effective to increase hip BMD by at least about 1% more preferably at least about 1.2% compared to pretreatment measurements. Such an increase in BMD may correspond to an increase of at least about 1.5%, about 1.6% or about 1.75% or more compared to untreated subjects in the same patient population over the same treatment period.

BMD in human subjects may be determined clinically using e.g. dual x-ray absorptiometry (DXA), for example of the hip. Other suitable techniques include, without limitation, ultrasonography, single energy x-ray absorptiometry (SXA) and quantitative computed tomography (OCT). Central skeletal sites can be measured such as the spine and hip and/or peripheral sites may be measured such as the forearm, finger, wrist or heel. These techniques involve comparison of the obtained results to one or more normative databases.

In other embodiments, the present invention provides a method for preventing or treating a bone-related disorder in a subject by administering a composition comprising an amount of trans-clomiphene or an analog or salt thereof in an amount effective to prevent or treat the disorder. In one aspect, the composition is administered to a human subject suffering from a bone related disorder selected from the group consisting of achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multi-system inflammatory disease, Winchester Syndrome, Menkes Disease, Wilson's Disease, ischemic bone disease (such as Legg-Calve-Perthes disease and regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, and skull bone loss associated with aging. In preferred embodiments, the composition is administered to a human in order to treat or prevent osteoporosis or osteopenia. In related embodiments, the human is a human male with low or low normal testosterone such as a secondary hypogonadal male. In related aspects, the amount of trans-clomiphene or an analogue or salt thereof is effective to reduce the level of a marker of bone resorption such as CTX by at least 5%, more preferably by at least 10%, most preferably by at least 15% compared to serum levels absent treatment.

It is to be understood that the methods of the invention need not cure a subject of a bone-related disorder or completely protect against the onset of a bone-related disorder to achieve a therapeutically beneficial response. The methods may be used prophylactically, meaning to protect, in whole or in part, against a bone-related disorder or symptom thereof. The methods may also be used therapeutically to ameliorate, in whole or in part, a bone related disorder or symptom thereof, or to protect, in whole or in part, against further progression of a bone-related disorder or symptom. The present methods are useful for increasing BMD and maintaining increased BMD over time and therefore are particularly useful for preventing the onset of osteopenia, preventing the progression of osteopenia to osteoporosis and for treating osteopenia and osteoporosis.

The family of triphenylalkylene derivatives representing analogs of clomiphene is defined here to include all unmodified trans forms, as well as each of the 4-hydroxylated, the N-dealkylated and the 4-hydroxy-N-dealkylated analogs of trans-clomiphene, as well as all other molecules with substantially similar structures. Analogs of trans-clomiphene such as those described in Ernst, et al., J. Pharmaceut. Sci. 65:148 (1976) and the metabolites described herein are also useful in the practice of the present invention.

In some embodiments, the subject in need of treatment by any of the methods of the present invention is a secondary hypogonadal male. In related embodiments, the subject in need of treatment by any of the methods of the present invention is a human male with a body mass index of at least 20, at least 21, at 22, at least 23, at least 24, at least 25, at least 26, at least 27, at least 28, at least 29, at least 30, at least 31 or at least 32. For example, the subject in need of treatment may be a human male with a body mass index of at least 25.

In related embodiments, the subject in need of treatment by any of the methods of the present invention is a human male or female with type 2 diabetes in which case the compositions of the invention are preferentially administered as part of a dosage regimen designed to reduce the risk of bone fractures. In one embodiment, the subject is a human male with type 2 diabetes and trans-clomiphene or an analogue or salt thereof is co-administered sequentially or simultaneously to the subject with metformin, phenformin, or buformin.

In a preferred embodiment, compositions of the invention comprise trans-clomphene or a salt thereof such as trans-clomiphene citrate at a dose which may range from 1 to 200 mg or from 5 to 100 mg. The dosage of trans-clomphene may also be from 5 to 10 mg, from 5 to 12.5 mg, from 5 to 15 mg, from 5 to 20 mg, from 10 to 15 mg, from 10 to 20 mg, from 12.5 to 25 mg, from 12.5 to 50 mg, or from 25 mg to 50 mg. The dosage of trans-clomphene may also be 12.5 mg, 25 mg or 50 mg.

In one embodiment, compositions of the invention comprise one or more pharmaceutically acceptable salts of trans-clomiphene or an analogue thereof. Depending on the process conditions the salt compound obtained may be either in neutral or salt form. Salt forms include hydrates and other solvates and also crystalline polymorphs. Both the free base and the salts of these end products may be used in accordance with the invention.

Acid addition salts may be transformed into the free base using basic agents such as alkali or by ion exchange. The free base obtained may also form salts with organic or inorganic acids.

In the preparation of acid addition salts, preferably such acids are used which form suitably pharmaceutically acceptable salts. Examples of such acids are hydrochloric acid, sulfuric acid, phosphoric acid, nitric acid, aliphatic acid, alicyclic carboxylic or sulfonic acids, such as formic acid, acetic acid, propionic acid, succinic acid, glycolic acid, lactic acid, malic acid, tartaric acid, citric acid, ascorbic acid, glucuronic acid, fumaric acid, maleic acid, hydroxymaleic acid, pyruvic acid, aspartic acid, glutamic acid, p-hydroxybenzoic acid, embonic acid, ethanesulfonic acid, hydroxyethanesulfonic acid, phenylacetic acid, mandelic acid, alogenbensenesulfonic acid, toluenesulfonic acid, galactaric acid, galacturonic acid or naphthalenesulfonic acid. All crystalline form polymorphs may be used in accordance with the invention. A preferred salt is the citrate salt.

Base addition salts may also be used in accordance with the invention and may be prepared by contacting the free acid form with a sufficient amount of the desired base to produce the salt in the conventional manner. The free acid form may be regenerated by contacting the salt form with an acid and isolating the free acid in the conventional manner. Pharmaceutically acceptable base addition salts are formed with metals or amines, such as alkali and alkali earth metals or organic amines. Examples of metals used as cations are sodium, potassium, calcium, magnesium and the like. Examples of suitable amines are amino acids such as lysine, choline, diethanolamine, ethylenediamine, N-methylglucamine and the like.

Compositions of the instant invention can be prepared in the form of a dose unit or dose units suitable for oral, parenteral, transdermal, rectal, transmucosal, or topical administration. Parenteral administration includes, but is not limited to, intravenous, intraarterial, intraperitoneal, subcutaneous, intramuscular, intrathecal, and intraarticular. Preferably, compositions of the instant invention are prepared in a form suitable for oral administration.

The terms "oral administration" or "orally deliverable" herein include any form of delivery of a therapeutic agent or a composition thereof to a subject wherein the agent or composition is placed in the mouth of the subject, whether or not the agent or composition is swallowed. Thus, "oral administration" includes buccal and sublingual as well as esophageal (e.g. inhalation) administration.

In still another embodiment, compositions of the present invention are formulated as rectal suppositories, which may contain suppository bases including, but not limited to, cocoa butter or glycerides.

Compositions of the present invention may also be formulated for inhalation, which may be in a form including, but not limited to, a solution, suspension, or emulsion that may be administered as a dry powder or in the form of an aerosol using a propellant, such as dichlorofuoromethane or trichlorofluoromethane.

Compositions of the present invention may also be formulated for transdermal delivery, for example as a cream, ointment, lotion, paste, gel, medicated plaster, patch, or membrane. Such compositions can comprise any suitable excipients, for example penetration enhancers and the like.

Compositions of the present invention may also be formulated for parenteral administration including, but not limited to, by injection or continuous infusion. Formulations for injection may be in the form of suspensions, solutions, or emulsions in oily or aqueous vehicles. Such compositions may also be provided in powder form for reconstitution with a suitable vehicle including, but not limited to, sterile, pyrogen-free water, WFI, and the like.

Compositions of the present invention may also be formulated as a depot preparation, which may be administered by implantation or by intramuscular injection. Such compositions may be formulated with suitable polymeric or hydrophobic materials (as an emulsion in an acceptable oil, for example), ion exchange resins, or as sparingly soluble derivatives (as a sparingly soluble salt, for example).

Compositions of the present invention may also be formulated as a liposome preparation. Liposome preparations can comprise liposomes which penetrate the cells of interest or the stratum corneum and fuse with the cell membrane resulting in delivery of the contents of the liposome into the cell. For example, liposomes such as those described in U.S. Pat. No. 5,077,211 to Yarosh, U.S. Pat. No. 4,621,023 to Redziniak et al., or U.S. Pat. No. 4,508,703 to Redziniak et al. can be used.

A composition of the invention can be in the form of solid dosage units such as tablets, (e.g. suspension tablets, bite suspension tablets, rapid dispersion tablets, chewable tablets, effervescent tablets, bilayer tablets, etc.), caplets, capsules (e.g., a soft or a hard gelatin capsule), powder (e.g. a packaged powder, a dispensable powder or an effervescent powder), lozenges, sachets, cachets, troches, pellets, granules, microgranules, encapsulated microgranules, powder aerosol formulations, or any other solid dosage form reasonably adapted for administration. A preferable dosage form is a soft or hard gelatin capsule. Another preferable dosage form is a tablet.

Tablets can be prepared according to any of the many relevant, well known pharmacy techniques. In one embodiment, tablets or other solid dosage forms can be prepared by processes that employ one or a combination of methods including, without limitation, (1) dry mixing, (2) direct compression, (3) milling, (4) dry or non-aqueous granulation, (5) wet granulation, or (6) fusion.

The individual steps in the wet granulation process of tablet preparation typically include milling and sieving of the ingredients, dry powder mixing, wet massing, granulation and final grinding. Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). Typically, no wet binder or moisture is involved in any of the steps.

In another embodiment, solid dosage forms can be prepared by mixing an antiestrogen with one or more pharmaceutical excipients to form a substantially homogenous preformulation blend. The preformulation blend can then be subdivided and optionally further processed (e.g. compressed, encapsulated, packaged, dispersed, etc.) into any desired dosage forms.

Compressed tablets can be prepared by compacting a powder or granulation composition of the invention. The term "compressed tablet" generally refers to a plain, uncoated tablet suitable for oral ingestion, prepared by a single compression or by pre-compaction tapping followed by a final compression. Tablets of the present invention may be coated or otherwise compounded to provide a dosage form affording the advantage of improved handling or storage characteristics. In one embodiment, any such coating will be selected so as to not substantially delay onset of therapeutic effect of a composition of the invention upon administration to a subject. The term "suspension tablet" as used herein refers to a compressed tablet that rapidly disintegrates after placement in water.

Suitable liquid dosage forms of a composition of the invention include solutions, aqueous or oily suspensions, elixirs, syrups, emulsions, liquid aerosol formulations, gels, creams, ointments, etc. Such compositions may also be formulated as a dry product for constitution with water or other suitable vehicle before use.

In one embodiment, liquid or semi-solid compositions, upon storage in a closed container maintained at either room temperature, refrigerated (e.g. about 5-10 C) temperature, or freezing temperature for a period of about 1, 2, 3, 4, 5, 6, 7, 8, 9, 10, 11, or 12 months, exhibit at least about 90%, at least about 92.5%, at least about 95%, or at least about 97.5% of the original antiestrogen compound present therein.

Compositions of the invention can, if desired, include one or more pharmaceutically acceptable excipients. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition. Excipients include, by way of illustration and not limitation, diluents, disintegrants, binding agents, adhesives, wetting agents, lubricants, glidants, surface modifying agents or surfactants, fragrances, suspending agents, emulsifying agents, nonaqueous vehicles, preservatives, antioxidants, adhesives, agents to adjust pH and osmolarity (e.g. buffering agents), preservatives, thickening agents, sweetening agents, flavoring agents, taste masking agents, colorants or dyes, penetration enhancers and substances added to improve appearance of the composition.

Excipients optionally employed in compositions of the invention can be solids, semi-solids, liquids or combinations thereof. Compositions of the invention containing excipients can be prepared by any known technique of pharmacy that comprises mixing an excipient with a drug or therapeutic agent.

Compositions of the invention optionally comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; and the like. Such diluents, if present, constitute in total about 5% to about 99%, about 10% to about 85%, or about 20% to about 80%, of the total weight of the composition. Any diluent or diluents selected preferably exhibit suitable flow properties and, where tablets are desired, compressibility.

The use of extragranular microcrystalline cellulose (that is, microcrystalline cellulose added to a wet granulated composition after a drying step) can be used to improve hardness (for tablets) and/or disintegration time.

Compositions of the invention optionally comprise one or more pharmaceutically acceptable disintegrants as excipients, particularly for tablet, capsule or other solid formulations. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, xanthan, locust bean, karaya, pectin and tragacanth gums.

Disintegrants may be added at any suitable step during the preparation of the composition, particularly prior to a granulation step or during a lubrication step prior to compression. Such disintegrants, if present, constitute in total about 0.2% to about 30%, about 0.2% to about 10%, or about 0.2% to about 5%, of the total weight of the composition.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, about 0.75% to about 15%, or about 1% to about 10%, of the total weight of the composition.

Compositions of the invention optionally comprise one or more pharmaceutically acceptable wetting agents as excipients. Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the composition.

Compositions of the invention optionally comprise one or more pharmaceutically acceptable lubricants (including anti-adherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition.

Suitable anti-adherents include talc, cornstarch, DL-leucine, sodium lauryl sulfate and metallic stearates. Talc is an anti-adherent or glidant used, for example, to reduce formulation sticking to equipment surfaces and also to reduce static in the blend. One or more anti-adherents, if present, constitute about 0.1% to about 10%, about 0.25% to about 5%, or about 0.5% to about 2%, of the total weight of the composition.

Glidants can be used to promote powder flow of a solid formulation. Suitable glidants include colloidal silicon dioxide, starch, talc, tribasic calcium phosphate, powdered cellulose and magnesium trisilicate. Colloidal silicon dioxide is particularly preferred.

Compositions of the present invention can comprise one or more anti-foaming agents. Simethicone is an illustrative anti-foaming agent. Anti-foaming agents, if present, constitute about 0.001% to about 5%, about 0.001% to about 2%, or about 0.001% to about 1%, of the total weight of the composition.

Illustrative antioxidants for use in the present invention include, but are not limited to, butylated hydroxytoluene, butylated hydroxyanisole, potassium metabisulfite, and the like. One or more antioxidants, if desired, are typically present in a composition of the invention in an amount of about 0.01% to about 2.5%, for example about 0.01%, about 0.05%, about 0.1%, about 0.5%, about 1%, about 1.5%, about 1.75%, about 2%, about 2.25%, or about 2.5%, by weight.

In various embodiments, compositions of the invention can comprise a preservative. Suitable preservatives include, but are not limited to, benzalkonium chloride, methyl, ethyl, propyl or butylparaben, benzyl alcohol, phenylethyl alcohol, benzethonium, methyl or propyl p-hydroxybenzoate and sorbic acid or combinations thereof. Typically, the optional preservative is present in an amount of about 0.01% to about 0.5% or about 0.01% to about 2.5%, by weight.

In one embodiment, compositions of the invention optionally comprise a buffering agent. Buffering agents include agents that reduce pH changes. Illustrative classes of buffering agents for use in various embodiments of the present invention comprise a salt of a Group IA metal including, for example, a bicarbonate salt of a Group IA metal, a carbonate salt of a Group IA metal, an alkaline or alkali earth metal buffering agent, an aluminum buffering agent, a calcium buffering agent, a sodium buffering agent, or a magnesium buffering agent. Suitable buffering agents include carbonates, phosphates, bicarbonates, citrates, borates, acetates, phthalates, tartrates, succinates of any of the foregoing, for example sodium or potassium phosphate, citrate, borate, acetate, bicarbonate and carbonate.

Non-limiting examples of suitable buffering agents include aluminum, magnesium hydroxide, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, tripotassium phosphate, trisodium phosphate, and trometamol. (Based in part upon the list provided in The Merck Index, Merck & Co. Rahway, N.J. (2001)). Furthermore, combinations or mixtures of any two or more of the above mentioned buffering agents can be used in the pharmaceutical compositions described herein. One or more buffering agents, if desired, are present in compositions of the invention in an amount of about 0.01% to about 5% or about 0.01% to about 3%, by weight.

In various embodiments, compositions the invention may include one or more agents that increase viscosity. Illustrative agents that increase viscosity include, but are not limited to, methylcellulose, carboxymethylcellulose sodium, ethylcellulose, carrageenan, carbopol, and/or combinations thereof. Typically, one or more viscosity increasing agents, if desired, are present in compositions of the invention in an amount of about 0.1% to about 10%, or about 0.1% to about 5%, by weight.

In various embodiments, compositions of the invention comprise an "organoleptic agent" to improve the organoleptic properties of the composition. The term "organoleptic agent" herein refers to any excipient that can improve the flavor or odor of, or help mask a disagreeable flavor or odor of a composition of the invention. Such agents include sweeteners, flavoring agents and/or taste masking agents. Suitable sweeteners and/or flavoring agents include any agent that sweetens or provides flavor to a pharmaceutical composition. Optional organoleptic agents are typically present in a composition of the invention in an amount of about 0.1 mg/ml to about 10 mg/ml, about 0.5 mg/ml to 5 mg/ml or about 1 mg/ml.

Illustrative sweeteners or flavoring agents include, without limitation, acacia syrup, anethole, anise oil, aromatic elixir, benzaldehyde, benzaldehyde elixir, cyclodextrins, caraway, caraway oil, cardamom oil, cardamom seed, cardamom spirit, cardamom tincture, cherry juice, cherry syrup, cinnamon, cinnamon oil, cinnamon water, citric acid, citric acid syrup, clove oil, cocoa, cocoa syrup, coriander oil, dextrose, eriodictyon, eriodictyon fluidextract, eriodictyon syrup, aromatic, ethylacetate, ethyl vanillin, fennel oil, ginger, ginger fluidextract, ginger oleoresin, dextrose, glucose, sugar, maltodextrin, glycerin, glycyrrhiza, glycyrrhiza elixir, glycyrrhiza extract, glycyrrhiza extract pure, glycyrrhiza fluid extract, glycyrrhiza syrup, honey, iso-alcoholic elixir, lavender oil, lemon oil, lemon tincture, mannitol, methyl salicylate, nutmeg oil, orange bitter, elixir, orange bitter, oil, orange flower oil, orange flower water, orange oil, orange peel, bitter, orange peel sweet, tincture, orange spirit, orange syrup, peppermint, peppermint oil, peppermint spirit, peppermint water, phenylethyl alcohol, raspberry juice, raspberry syrup, rosemary oil, rose oil, rose water, stronger, saccharin, saccharin calcium, saccharin sodium, sarsaparilla syrup, sarsaparilla, sorbitol solution, spearmint, spearmint oil, sucrose, sucralose, syrup, thyme oil, tolu balsam, tolu balsam syrup, vanilla, vanilla tincture, vanillin, wild cherry syrup, or combinations thereof.

Illustrative taste masking agents include, but are not limited to, cyclodextrins, cyclodextrins emulsions, cyclodextrins particles, cyclodextrins complexes, or combinations thereof.

Illustrative suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats.

Illustrative emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol.

The foregoing excipients can have multiple roles as is known in the art. For example, starch can serve as a filler as well as a disintegrant. The classification of excipients above is not to be construed as limiting in any manner.

Compositions of the present invention may be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, intraarticular, intracisternal and intraventricular.

A therapeutically effective amount of the composition required for use in therapy varies with the length of time that activity is desired, and the age and the condition of the patient to be treated, among other factors, and is ultimately determined by the attendant physician. In general, however, doses employed for human treatment typically are in the range of about 0.001 mg/kg to about 500 mg/kg per day, for example about 1 µg/kg to about 1 mg/kg per day or about 1 µg/kg to about 100 µg/kg per day. For most large mammals, the total daily dosage is from about 1 to 100 mg, preferably from about 2 to 80 mg. The dosage regimen may be adjusted to provide the optimal therapeutic response. The desired dose may be conveniently administered in a single dose, or as multiple doses administered at appropriate intervals, for example as two, three, four or more subdoses per day.

Illustratively, a composition of the invention may be administered to a subject to provide the subject with an antiestrogen in an amount of about 1 µg/kg to about 1 mg/kg body weight, for example about 1 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg or about 1 mg/kg body weight.

In a preferred embodiment, compositions according to the present invention comprise trans-clomiphene at a dosage between one mg to about 200 mg (although the determination of optimal dosages is with the level of ordinary skill in the art). The composition may comprise trans-clomiphene at a dosage of about 1 mg, 2 mg, 3 mg, 4 mg, 5 mg, 10 mg, 12 mg, 12.5 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg or there between. The composition is preferably substantially free of cis-clomiphene and may comprise 0% w/w cis-cloimphene. Analogs of the trans-isomer of clomiphene such as those described in Ernst, et al. supra are also useful in the practice of the present invention.

Compositions of the present invention may also be administered long-term. In this regard, the compositions may be administered for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. The compositions may also be administered for an administration period of at least 1, 2, 3, 4, 5, 6, 7, 8, 9, 10, 11, 12 or more months. The compositions may also be administered for an administration period of at least 1, 2, 3, 4, 5, 6, 7, 8, 9, 10 or more years. During the administration period, the composition may be administered daily or periodically such as every other day and the like.

Compositions of the present invention may also be administered intermittently. For example, the compositions may be administered for an administration period of 1, 2, 3, 4, 5, or more weeks, followed by a period of discontinuance, followed by an administration period of 1, 2, 3, 4, 5 or more weeks, and so on.

All of the references referred to herein are incorporated by reference in their entirety.

The following Examples are meant to be illustrative of the invention and are not intended to limit the scope of the invention as set out is the appended claims.

EXAMPLE 1

Effects of Trans-Clomiphene and Exogenous Testosterone Treatment on Serum Markers of Bone Resorption The effect of the isolated trans-clomiphene isomer on the serum level of biomarkers of bone resorption was assessed in human males with secondary hypogonadism.

Adult male subjects with a morning total testosterone blood level of <300 ng/dl and a serum LH of <15 IU/ml were administered either trans-clomiphene (12 mg/day or 25 mg/day via oral capsule) or a topical testosterone gel (Testim®, 50 mg applied daily) over a three month period. Quantitative determination of baseline serum (circulating) estrogen (E2), dihydrotestosterone (DHT), sex hormone binding globulin (SHBG), P1NP-1 and CTX measurements were made in the subjects by immunoassay. Treatment with either trans-clomiphene (12.5 mg or 25 mg) or Testim® was then initiated. Follow-up measurements were taken at 3 weeks post initial dose, 6 months post initial dose and one month after cessation of treatment. The results are presented below at Table 1:

TABLE 1

| | Effect of treatment on serum hormone and SHBG levels | | | | | | | |
|---|---|---|---|---|---|---|---|---|
| Group | Baseline (before TxT) | | 6 weeks | | 3 months | | Post TxT | |
| | DHT† | SD | DHT | SD | DHT | SD | DHT | SD |
| 12.5 mg Androxal | 15 | 4.6 | 22.7*^ | 9.6 | 20.4^ | 9.1 | 13.7 | 4.3 |
| 25 mg Androxal | 15.3 | 7.2 | 22.2*^ | 9.8 | 23.2*^ | 20.2 | 15.8 | 5.4 |

TABLE 1-continued

Effect of treatment on serum hormone and SHBG levels

| Group | Baseline (before TxT) | | 6 weeks | | 3 months | | Post TxT | |
|---|---|---|---|---|---|---|---|---|
| Testim | 14.7 | 5.1 | 59.2*¶ | 36.3 | 51.6*¶ | 37.7 | 19.6 | 22.7 |
| Placebo | 14.4 | 4.5 | 17.7 | 14.9 | 15.8 | 7.8 | 20.1 | 27.9 |
| | E2‡ | SD | E2 | SD | E2 | SD | E2 | SD |
| 12.5 mg Androxal | 20.8 | 12.4 | 52.1*¶ | 35.3 | 56.7*¶ | 31.5 | 39.1* | 24.2 |
| 25 mg Androxal | 24.7 | 15.9 | 48.3*¶ | 28.3 | 46.3*¶ | 30.7 | 40.2* | 27.4 |
| Testim | 26.3 | 21.8 | 44.2*¶ | 27.1 | 37.9*¶ | 21.7 | 29 | 16.6 |
| Placebo | 22.3 | 15 | 26.5 | 20.3 | 23.9 | 17.9 | 33.3 | 26.1 |
| | SHBG§ | SD | SHBG | SD | SHBG | SD | SHBG | SD |
| 12.5 mg Androxal | 24.7 | 12.9 | 28.6 | 14.8 | 29.3 | 15.2 | 24.9 | 15.2 |
| 25 mg Androxal | 26.4 | 12.1 | 32 | 14.5 | 29.5 | 12.2 | 28.7 | 12.3 |
| Testim | 26.1 | 10.5 | 24.6 | 10.3 | 25.2 | 9.8 | 27.9 | 16.7 |
| Placebo | 27.7 | 15.5 | 29.3 | 16.6 | 31.4 | 19.2 | 26.8 | 11 |

*different vs. before TxT
^different vs. Testim
¶different vs. Placebo
†ng/DL
‡pg/mL
§nmoles/L A significant increase was observed in serum estradiol 17β (E2) following daily administration of trans-clomiphene for 6 weeks and 3 months. Testim®, topical exogenous testosterone, raised serum estrogen to an equal extent as trans-clomiphene and raised DHT to a greater extent than trans-clomiphene. Serum estrogen levels remained elevated after cessation of treatment with trans-clomiphene compared with baseline. The relative stability of the SHBG level during treatment suggested that no changes in free testosterone or estrogen occurred given that SHBG binds both testosterone and estrogen in the serum Importantly, no differentiation on the ability of trans-clomiphene to raise estradiol levels was observed compared to Testim®.

Figure 1:
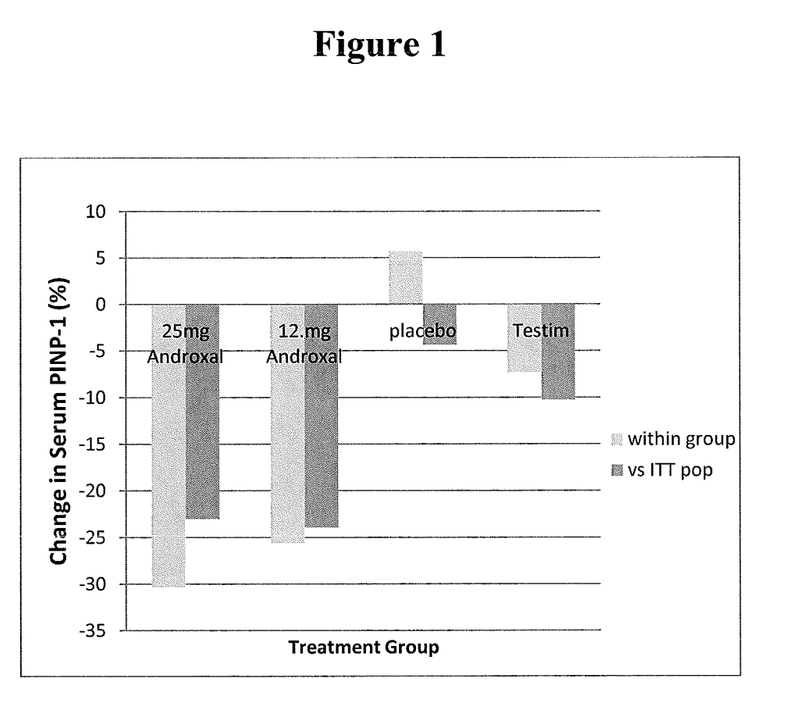
FIG. 1 demonstrates the effect of Androxal™ (trans-clomiphene) and Testim® on serum P1NP-1 levels FIG. 2 demonstrates the effect of Androxal™ (trans-clomiphene) and Testim® on serum CTX levels FIG. 3 demonstrates the change in total hip bone mineral density (BMD) after 6 months of treatment with Androxal™ (trans-clomiphene).
Figure 2:
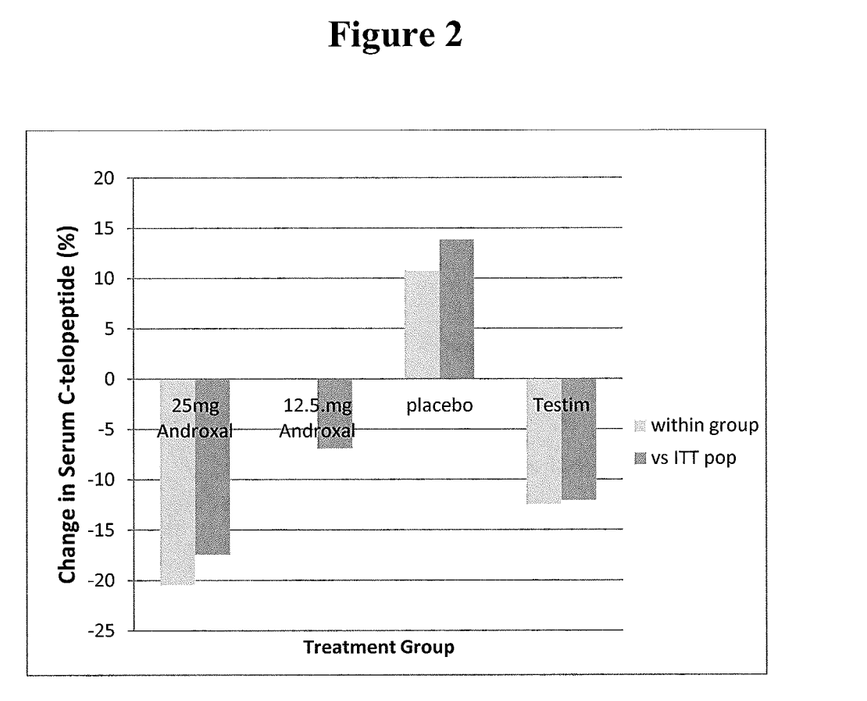

The effects of trans-clomiphene and Testim® on the level of serum biomarkers of bone formation (P1NP) and bone resorption (CTX) are illustrated at FIGS. 1 and 2. A decrease in serum P1NP-1 levels was observed in subjects treated at either dose of trans-clomiphene; however, no changes or slight increases were observed in the control and Testim® groups (FIG. 1). The inability to lower P1NP-1 simply by increasing testosterone by way of Testim® treatment demonstrates a striking difference in comparison to the action of trans-clomiphene. A dose dependency in the decrease in P1NP-1 levels was observed, with the 25 mg dose exhibiting a more robust decrease than the 12.5 mg dose. The lower levels of P1NP-1 at both trans-clomiphene doses are well within the normal range (15-80 µg/L). A decrease in CTX levels was also observed at both trans-clomiphene dosages; however, the decrease was much stronger at the 25 mg dose. In contrast, a significant increase in CTX levels relative to baseline was observed in control subjects. The Testim®-treated group exhibited a moderate decrease in CTX levels. The changes in serum biomarkers were the same according to intention-to-treat (ITT) analysis, despite the ITT population containing drop-outs.

The decreases in P1NP-1 and CTX observed with trans-clomiphene treatment did not appear to be associated with the level of serum testosterone, DHT or estrogen (Table 1) given that the individual treatments were not significantly different in those hormonal effects yet trans-clomiphene demonstrated stronger decreases of these biomarkers at the 25 mg per day dose. Surprisingly, it appears that trans-clomiphene and Testim® exert their effects on bone by different mechanisms.

Figure 3:
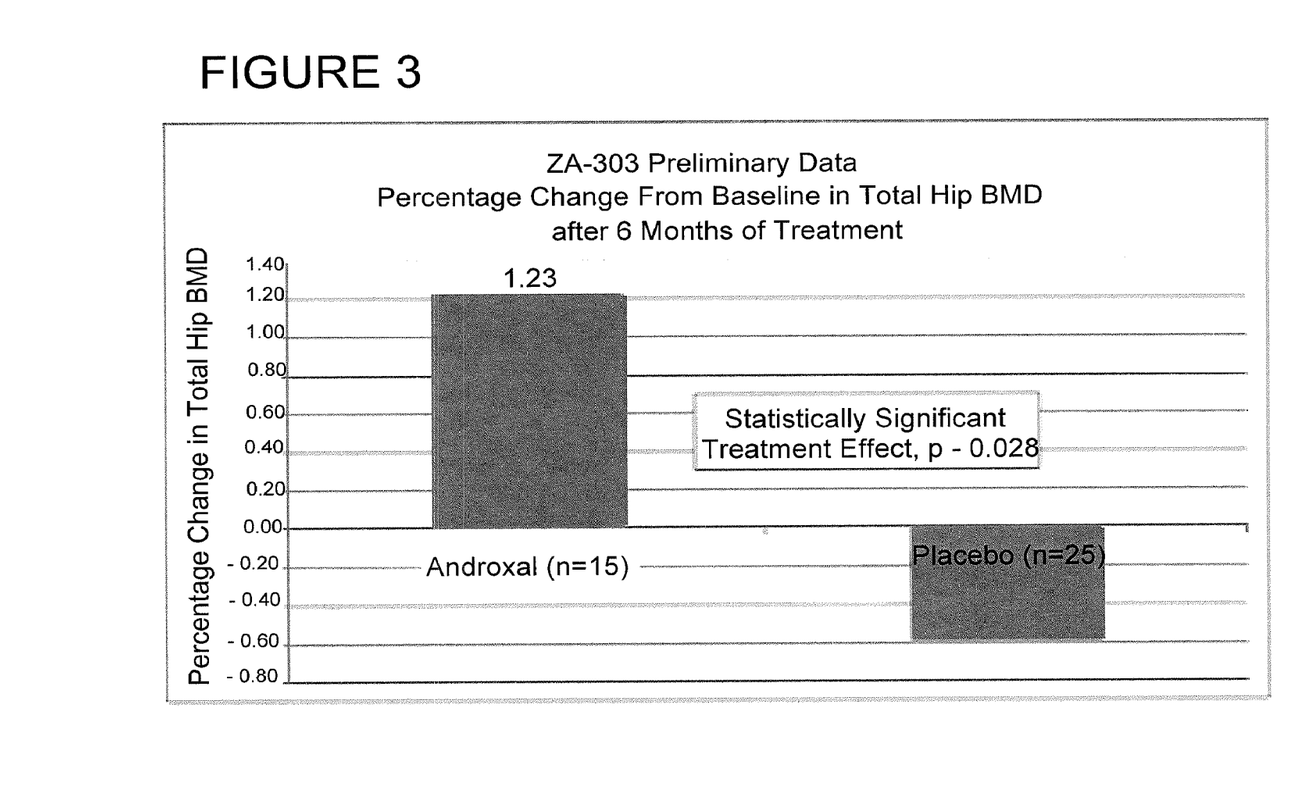

The effect of trans-clomiphene on total hip bone mineral density (BMD) was assessed by dual-energy x-ray absorptiometry (DEXA) scans in 15 hypogonadal males (morning testosterone less than 300 ng/dL) with body mass index (BMI) ranging between 25 and 42 and no evidence of bone disease (including ostepenia) prior to treatment. DEXA scans were performed prior to treatment with trans-clomiphene to determine baseline measurements and after 6 months of daily administration of trans-clomiphene. Four of the 15 subjects received 12.5 mg trans-clomiphene administered daily throughout the 6 month period. Eleven of the 15 subjects began at the 12.5 mg/day dose but were later up-titrated to 25 mg/day. Total hip BMD was also assessed in 25 placebo (control) subjects at the same time points. BMD measurements at the 6 month time point in both treated and control subjects were compared to baseline measurements. The results are presented in FIG. 3. An increase of about 1.23% in hip BMD was observed in subjects treated with trans-clomiphene during the 6 month period, confirming the ability of trans-clomiphene to increase BMD. Control (placebo) subjects, on the other hand, exhibited a 0.59% decrease in BMD over the same time period.

Discussion

Together, these results indicate that trans-clomiphene significantly lowers the serum level of biomarkers of bone resorption and bone formation and that this reduction in bone formation occurs by a mechanism apparently distinct from that of testosterone and this inhibition of bone turnover is associated with increased bone mineral density thereby indicating that trans-clomiphene and its analogues are useful for treating a variety of bone disorders.

EXAMPLE 2

Inhibiting Bone Resorption Using Trans-Clomiphene or an Analogue or Salt Thereof Subjects having a need or desire to reduce bone resorption (e.g. in order to increase bone mineral density, reduce the likelihood of bone fractures, and/or prevent or treat one or more bone related disorders may be administered an effective amount of trans-clomiphene (or a salt or analogue thereof) over a treatment period of sufficient duration to achieve the desired result. In this case, one or more biomarkers of bone resorption would be assessed prior to initiating treatment and then monitored through the course of treatment. By way of nonlimiting example, a subject at risk for or diagnosed with a bone related disorder is administered 5 mg to 100 mg trans-clomiphene daily or every other day for a treatment period of at least three months, preferably at least six months. A preferred biomarker of bone resorption useful according to the methods is CTX. Other biomarkers of bone resorption useful according to the methods include without limitation N-terminal telopeptide of type 1 collagen (NTX), deoxypyridinoline (DPD), pyridinoline, urinary hydroxyproline, galactosyl hydroxylysine, and tartrate-resistant acid phosphatase, although it is to be understood that any established biomarker of bone resorption can be used to assess bone resorption.

EXAMPLE 3

Inhibiting Bone Turnover Using Trans-Clomiphene or an Analogue or Salt Thereof

Subjects having a need or desire to reduce bone turnover (e.g. in order to increase bone mineral density, reduce the likelihood of bone fractures, and/or prevent or treat one or more bone related disorders may be administered an effective amount of trans-clomiphene (or a salt or analogue thereof) over a treatment period of sufficient duration to achieve the desired result. In this case, one or more biomarkers of bone resorption and one or more biomarkers of bone formation would be assessed prior to initiating treatment and then monitored through the course of treatment. By way of nonlimiting example, a subject at risk for or diagnosed with a bone related disorder is administered 5 mg to 100 mg trans-clomiphene daily or every other day for a treatment period of at least three months, preferably at least six months. Preferred biomarkers of bone resorption useful according to the methods include, without limitation, CTX, NTX, DPD, pyridinoline, urinary hydroxyproline, galactosyl hydroxylysine, and tartrate-resistant acid phosphatase. Preferred biomarkers of bone formation useful according to the methods include, without limitation P1NP, bone-specific alkaline phosphatase (BSAP) and osteocalcin (OstCa). It is to be understood, however, that any established biomarkers of bone resorption and bone formation can be used to assess bone turnover.

The invention claimed is:

1. A method for increasing bone mineral density (BMD) in a human male having or at risk for developing osteopenia or osteoporosis and at least 50 years of age with a body mass index (BMI) of at least 25 and a testosterone level below about 400 ng/dl, the method comprising administering to the subject a composition comprising trans-clomiphene or an analogue or pharmaceutically acceptable salt thereof, the composition being substantially free of cis-clomiphene, wherein the trans-clomiphene is administered in a daily amount of about 25 mg for a period of at least 6 months, whereby the serum level of CTX in the male is reduced by at least about 10% to 20% and the serum level of PINP in the human male is reduced by at least about 10% to 30%.

2. A method for preventing and/or treating osteopenia or osteoporosis in a human subject at least 50 years of age with a body mass index (BMI) of at least 25, the method comprising administering to the subject a composition comprising trans-clomiphene or an analogue or pharmaceutically acceptable salt thereof, the composition being substantially free of cis-clomiphene, wherein the trans-clomiphene is administered in a daily amount of about 25 mg for a period of at least 6 months.

3. The method of claim 2, wherein the one or more serum biomarkers of bone resorption comprises CTX.

4. The method of claim 3 wherein the composition is administered for a period of at least a year.

5. The method of claim 2 wherein the subject is a human male with a testosterone level below about 400 ng/dl.

6. The method of claim 5 wherein the male is a secondary hypogonadal male.

7. The method of claim 2 wherein the secondary hypogonadal human male is at least 60 years of age.

8. The method of claim 2 wherein the composition comprises trans-clomiphene or a pharmaceutically acceptable salt thereof and comprises 0% w/w of cis-clomiphene.

9. The method of claim 3, wherein the male has a testosterone level below about 400 ng/dl.

10. The method of claim 9, wherein the male is a secondary hypogonadal male.

11. The method of claim 3, wherein the composition comprises trans-clomiphene or a pharmaceutically acceptable salt thereof and comprises 0% w/w of cis-clomiphene.

12. The method of claim 2, wherein the male is between 50 years of age and 60 years of age.

* * * * *